United States Patent
Geiger

(10) Patent No.: US 10,709,851 B2
(45) Date of Patent: Jul. 14, 2020

(54) SYSTEMS, METHODS AND DEVICES FOR SUBCUTANEOUS TARGET LOCATION

(71) Applicant: SIENTRA, INC., Santa Barbara, CA (US)

(72) Inventor: Steven Charles Geiger, Hamilton, MT (US)

(73) Assignee: SIENTRA, INC., Santa Barbara, CA (US)

( * ) Notice: Subject to any disclaimer, the term of this patent is extended or adjusted under 35 U.S.C. 154(b) by 491 days.

(21) Appl. No.: 15/339,657

(22) Filed: Oct. 31, 2016

(65) Prior Publication Data

US 2017/0182263 A1 Jun. 29, 2017

Related U.S. Application Data

(60) Provisional application No. 62/247,800, filed on Oct. 29, 2015.

(51) Int. Cl.
| | | |
|---|---|---|
| *H01F 7/20* | (2006.01) | |
| *A61M 5/42* | (2006.01) | |
| *A61M 39/02* | (2006.01) | |
| *A61B 5/06* | (2006.01) | |
| *A61M 5/142* | (2006.01) | |
| *A61B 90/00* | (2016.01) | |

(52) U.S. Cl.
CPC ............. *A61M 5/427* (2013.01); *A61B 5/062* (2013.01); *A61M 5/14276* (2013.01); *A61M 39/0208* (2013.01); *A61B 2090/3958* (2016.02); *A61B 2562/16* (2013.01); *A61M 2005/14284* (2013.01); *A61M 2039/0238* (2013.01); *A61M 2205/6054* (2013.01)

(58) Field of Classification Search
CPC .................................................... A61B 5/062
USPC ....................................................... 335/285
See application file for complete search history.

(56) References Cited

U.S. PATENT DOCUMENTS

| | | | | |
|---|---|---|---|---|
| 4,222,374 A | * | 9/1980 | Sampson | A61M 39/0208 128/899 |
| 4,286,584 A | * | 9/1981 | Sampson | A61M 39/0208 128/899 |
| 7,255,682 B1 | * | 8/2007 | Bartol, Jr. | A61M 5/158 604/116 |
| 7,608,038 B2 | * | 10/2009 | Ginsberg | A61B 17/3403 600/104 |
| 8,171,938 B2 | * | 5/2012 | Bengtson | A61M 39/0208 128/899 |
| 8,454,690 B2 | | 6/2013 | McClellan | |
| 8,816,806 B2 | * | 8/2014 | Tait | H01F 7/021 335/285 |

(Continued)

*Primary Examiner* — Alexander Talpalatski
(74) *Attorney, Agent, or Firm* — Baker & McKenzie

(57) ABSTRACT

Embodiments of the invention provide devices, systems, and methods that precisely identify a minimum of one predetermined spot which is hidden under a skin. The system comprises a locator device and corresponding implanted target device. The port locator device preferably comprises one magnet with north and south magnetic pole, a body and a suspending component. The body may utilize specific geometry which improves accuracy. The implanted target device may include at least one magnet and at least one target or a plurality of targets and at least one magnet. Various configurations can be provided that precisely identify a single spot or a plurality of spots which are hidden under a skin.

15 Claims, 14 Drawing Sheets

(56) References Cited

U.S. PATENT DOCUMENTS

| | | | |
|---|---|---|---|
| 9,072,895 B2* | 7/2015 | Mate | A61N 5/1049 |
| 9,764,124 B2* | 9/2017 | Tallarida | A61M 39/0208 |
| 9,788,838 B2 | 10/2017 | McClellan et al. | |
| 10,010,404 B2 | 7/2018 | McClellan | |
| 10,588,737 B2 | 3/2020 | McClellan | |
| 2013/0325120 A1 | 12/2013 | McClellan | |
| 2015/0238118 A1* | 8/2015 | Legassey | A61B 5/062 |
| | | | 600/347 |

* cited by examiner

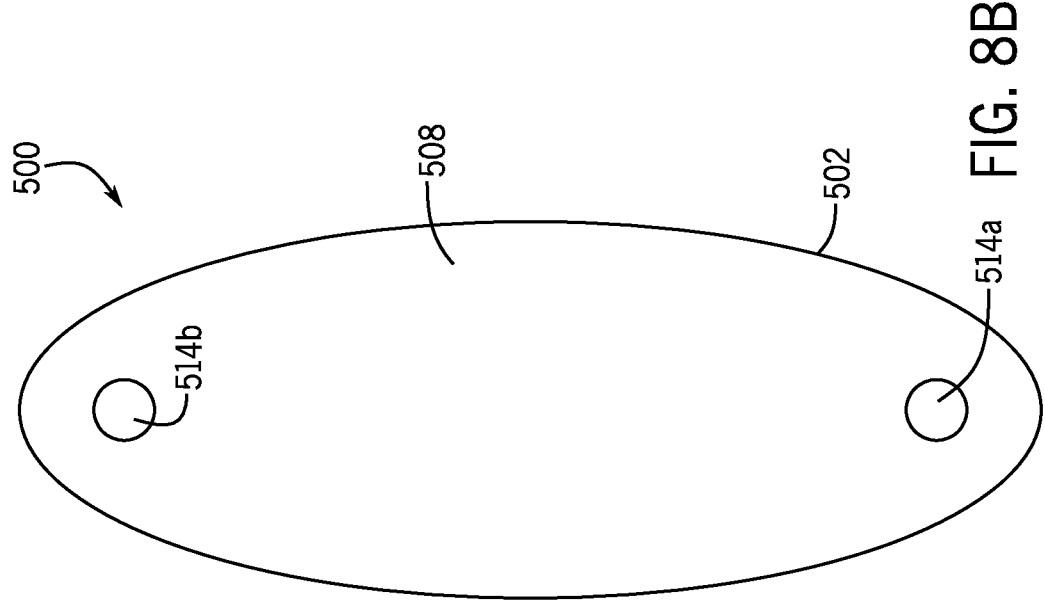
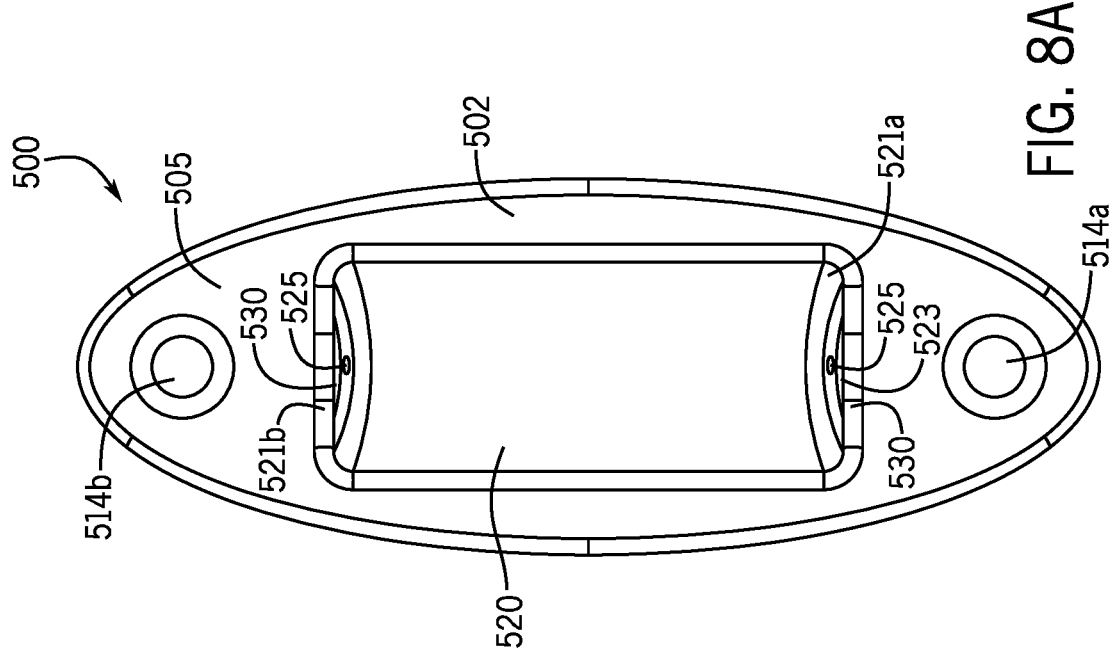

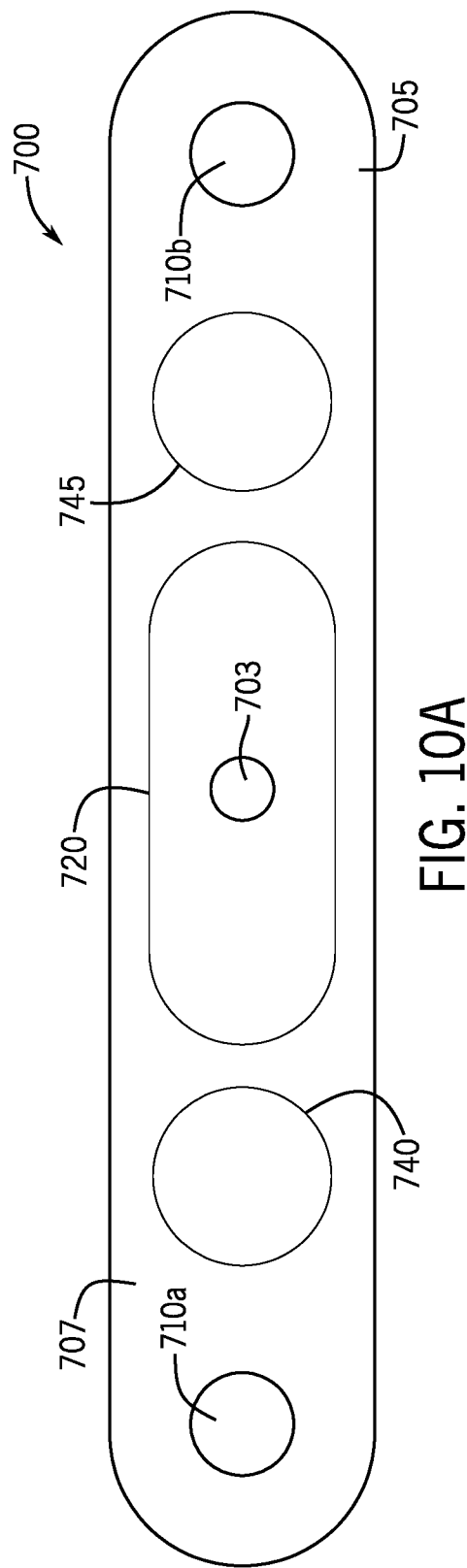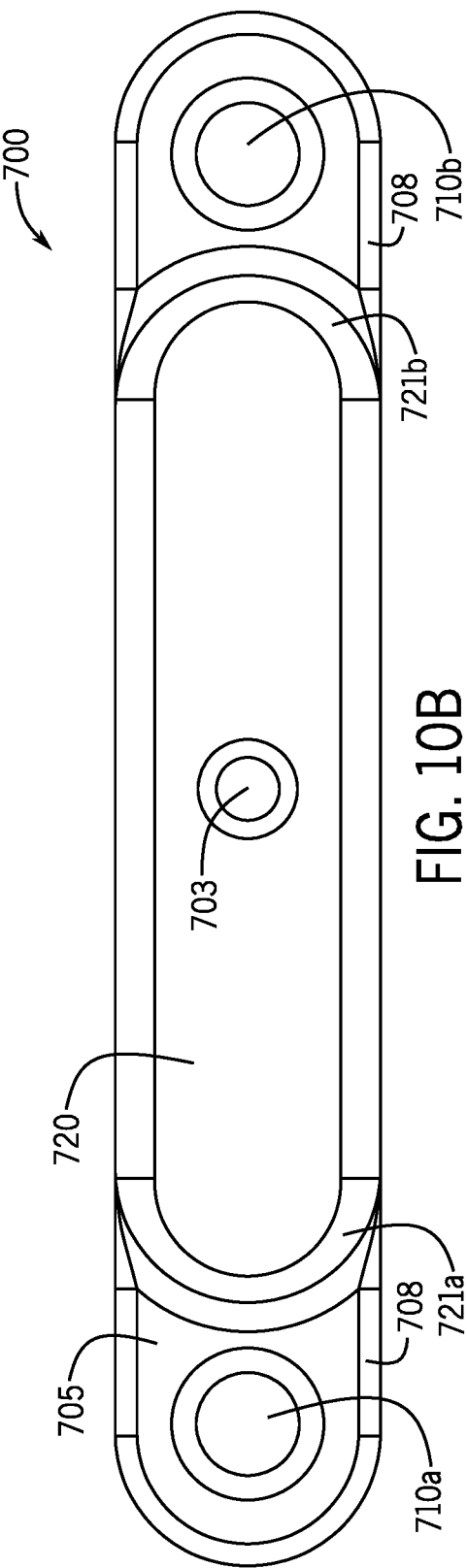
FIG. 10A
FIG. 10B

SYSTEMS, METHODS AND DEVICES FOR SUBCUTANEOUS TARGET LOCATION

RELATED APPLICATIONS

This application claims priority to U.S. provisional application Ser. No. 62/247,800, filed on Oct. 29, 2015, the entire contents of which are incorporated herein by reference.

BACKGROUND

Implantable medical devices, materials and structures sometimes require post-implant access. For example, tissue expanders used in reconstruction surgeries require highly accurate location of at least one predetermined access point under the skin. After locating a predetermined access point, the caregiver typically passes a syringe needle through the skin at the access point in order to access the tissue expander's insufflation port. Some implanted structures may have complex geometries and/or access locations may move or deform over time. Conversely, some implants can include a simple device geometry where it can be difficult to detect the exact access location (e.g., due to very small angular changes in and around the access location). Even when an access point is determined, location accuracy though thick tissue associated with high Body Mass Index (BMI) patients can adversely affect the ability to safely access the implant. Some locator devices include conventional magnet locators that generally include magnets with locator holes. However, precise vertical alignment of the magnet and access hole can be difficult to achieve, especially for patients with a high BMI. Further, some catheters and other medical devices and applications can include two or more hidden spots that must be precisely located. For example, in various medical applications including research there can be a need for a device which can precisely locate a device with more than two subcutaneous ports.

Thus, there is a need for a device which is sufficiently sensitive for patients with very thick tissue. The device would preferably precisely, accurately and concurrently locate a plurality of spots on or under skin without requiring a hole in the locator magnet. The would preferably not require a magnet dedicated to each target and not require any magnet to align over the physical perimeter of the target or targets.

SUMMARY

Some embodiments include a target location assembly comprising a base including a first infusion port positioned adjacent one end of the base, and a target magnet housing coupled to and extending from a first face of the base. The target magnet housing includes a first end positioned adjacent one end of the base and extending towards an opposite end of the base. A target magnet is positioned in the target magnet housing, and includes one magnetic pole adjacent the first end of the target magnet housing and a magnetically opposite pole adjacent the second end of the target magnet housing. The target location assembly includes a locator assembly with an elongated locator base, a first port aperture positioned adjacent one end of the locator base. Further, an upper housing is coupled to and extends from a first side of the locator base. The upper housing includes a first end positioned adjacent one end of the locator base and extends towards an opposite end of the locator base. Further, two locator magnets positioned at least partially within the upper housing adjacent each end of the locator housing.

In some embodiments, the base is elongated. In some further embodiments, the elongated base is ellipsoidal shaped, rectangular shaped, or oblong. In some embodiments, the target magnet housing is positioned generally centrally with respect to the base. In some embodiments, the target magnet housing is elongated. In some embodiments, the base includes a second infusion port positioned adjacent an opposite end of the base to the first infusion port.

In some embodiments of the invention, the target magnet housing includes at least one attachment aperture. In some embodiments, the attachment aperture comprises a channel extending a longitudinal length of the target magnet housing from each end of the target magnet housing. Some embodiments include a suspending guide extending from the upper housing away from the locator base. Some embodiments comprise a suspending line coupled to the suspending guide.

In some embodiments, the two locator magnets are positioned with respect to each other with reversed magnetic poles. In some further embodiments, at least one of the two locator magnets extend from a second side of the locator base and into a portion of the upper housing. In some embodiments, at least one of the two locator magnets is positioned extending through the second side of the locator base. In some further embodiments, one end of one of the two locator magnets extends from the second side of the locator base and away from the upper housing.

Some embodiments include a second port aperture positioned adjacent an end of the locator base opposite to the location of the first port aperture.

Some embodiments include a target locator system comprising a base including a first infusion port positioned adjacent one end of the base, and a target magnet coupled to a first side of the base, where the target magnet includes one magnetic pole adjacent one end of the base. Further, a locator assembly includes a locator base, and a port aperture is positioned adjacent one end of the locator base. Further, two locator magnets are positioned coupled to locator base adjacent opposite ends of the locator base, and the two locator magnets positioned with respect to each other with reversed magnetic poles.

Some embodiments include a second infusion port positioned adjacent an opposite end of the base to the first infusion port. Some embodiments include a second port aperture positioned adjacent an end of the locator base opposite to the location of the first port aperture.

Some further embodiments of the invention include a suspending guide extending from the locator base. In some embodiments, the two locator magnets extend from a second side of the locator base and through the first side of the locator base.

DESCRIPTION OF THE DRAWINGS

FIG. 8A illustrates a top view of the target assembly of FIGS. 7A-7B in accordance with some embodiments of the invention.

FIG. 8B illustrates a bottom view of the target assembly of FIGS. 7A-7B in accordance with some embodiments of the invention.

FIG. 10A illustrates a bottom view of the locator assembly of FIGS. 9A-9B in accordance with some embodiments of the invention FIG. 10B illustrates a top view of the locator assembly of FIGS. 9A-9B in accordance with some embodiments of the invention.

DETAILED DESCRIPTION

Figure 1A:
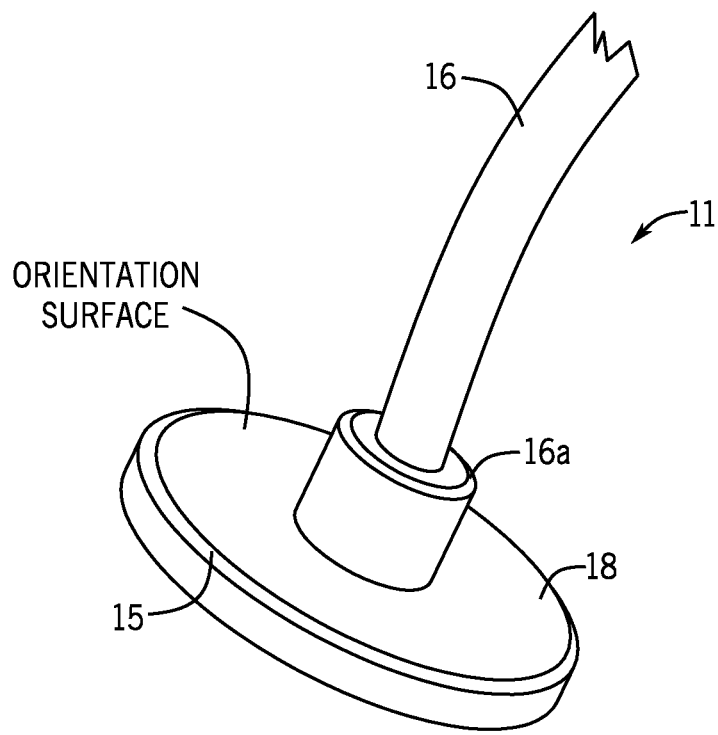
FIG. 1A shows a perspective view of a locator device with a locator magnet, body, suspending member and orientation surface in accordance with some embodiments of the invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives that fall within the scope of embodiments of the invention.

The invention generally relates to medical devices and procedures, and more particularly to subcutaneous magnetically locatable ports, devices, systems and methods for locating the same. Some embodiments of the invention can be applicable to veterinary fields or other fields of biology such as biological compatibility testing.

Figure 1B:
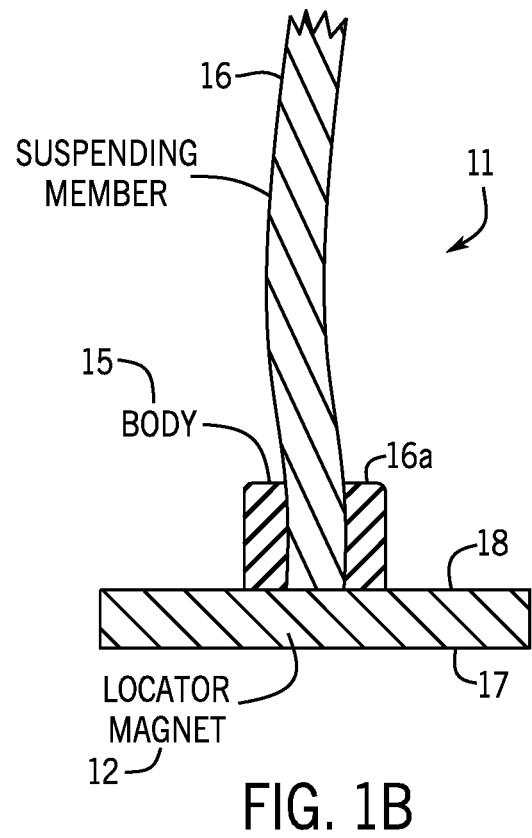
FIG. 1B shows a cross-sectional view of the locator device displayed in FIG. 1A with a locator magnet, body, suspending member and orientation surface in accordance with some embodiments of the invention.

FIG. 1A shows a perspective view of a locator device 11 according to some embodiments of the invention. In some embodiments, the locator device 11 includes a body 15 with suspending member 16 extending from collar 16a that is coupled to the orientation surface 18 in accordance with some embodiments of the invention. FIG. 1B shows a cross-sectional view of the locator device 11 displayed in FIG. 1A in accordance with some embodiments of the invention. In some embodiments, the locator device 11 includes locator magnet 12 positioned in the body 15 between the orientation surface 18 and the bottom surface 17.

Figure 2A:
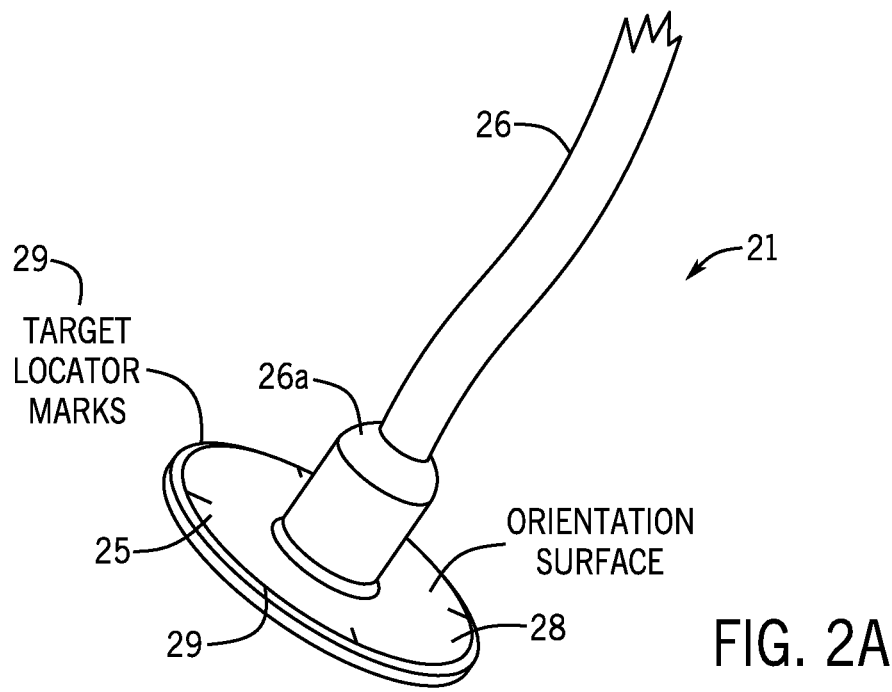
FIG. 2A shows a perspective view of a locator device with a locator magnet, body, suspending member and orientation surface in accordance with some embodiments of the invention.
Figure 2B:
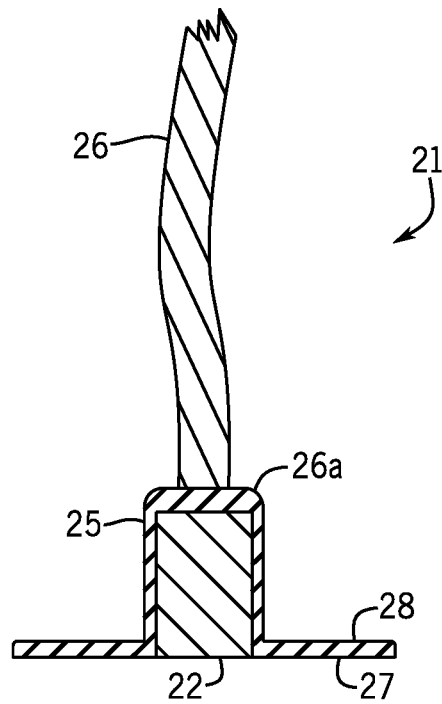
FIG. 2B shows a cross-sectional view of the locator device displayed in FIG. 2A with a locator magnet, body, suspending member and orientation surface in accordance with some embodiments of the invention.

FIG. 2A shows a perspective view of a locator device 21 in accordance with some further embodiments of the invention, and FIG. 2B shows a cross-sectional view of the locator device 21 displayed in FIG. 2A in accordance with some embodiments of the invention. In some embodiments, the locator device 21 includes a body 25 with suspending member 26 extending from upper surface 26a of the body 25 that is coupled to the orientation surface 28. In some embodiments, the locator device 21 includes locator magnet 22 positioned in the body 25 and positioned generally centrally within the orientation surface 28 and extending between the orientation surface 28 and the bottom surface 17. In some embodiments, the orientation surface 28 includes one or more target locator marks 29.

Figure 3A:
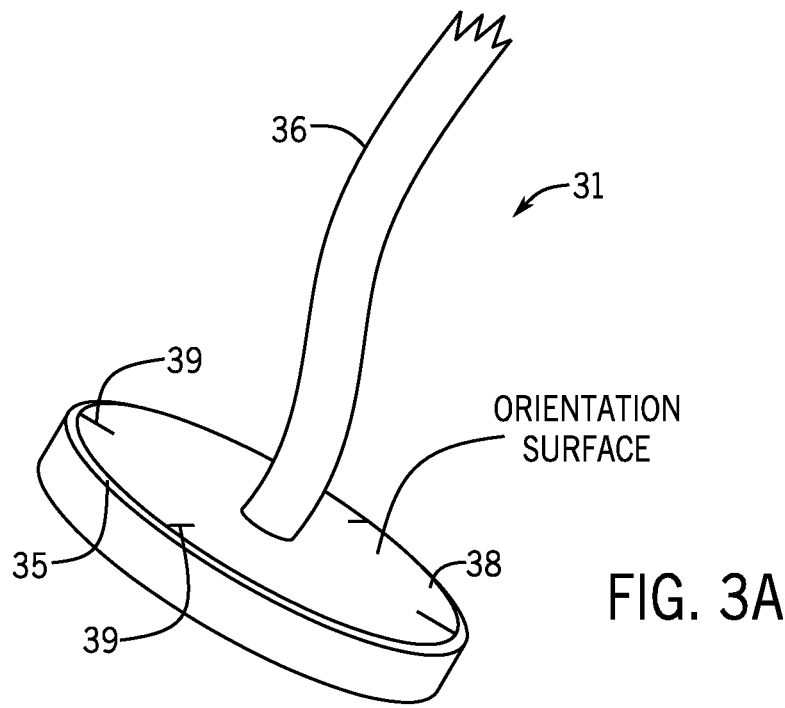
FIG. 3A shows a perspective view of a locator device with a locator magnet, body, suspending member and orientation surface in accordance with some embodiments of the invention.
Figure 3B:
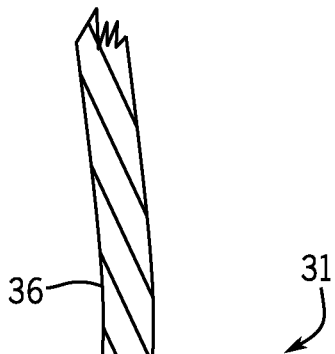
FIG. 3B shows a cross-sectional view of the locator device displayed in FIG. 3A with a locator magnet, body, suspending member and flat orientation surface in accordance with some embodiments of the invention.
Figure 3B:
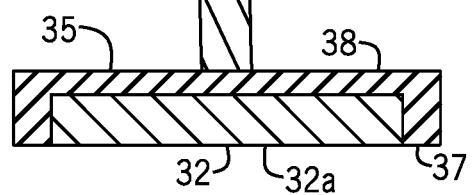

FIG. 3A shows a perspective view of a locator device 31 in accordance with some embodiments of the invention, and FIG. 3B shows a cross-sectional view of the locator device 31 displayed in FIG. 3A in accordance with some embodiments of the invention. In some embodiments, the locator device 31 includes a locator magnet 32 coupled to the body 35 between bottom surface 37 and orientation surface 38, and a suspending member 36 coupled to and extending from the orientation surface 38. In some embodiments, the orientation surface 38 includes target locator marks 39 for used for reference when marking the skin surface and subsequent location of the target center in accordance with some embodiments of the invention. As illustrated in the cross-sectional view of the locator device 31 shown in FIG. 3B, in some embodiments, the body 35 can at least partially surround the locator magnet 32, and the base surface 32a of the locator magnet 32 can be flush with the bottom surface 37.

Figure 4A:
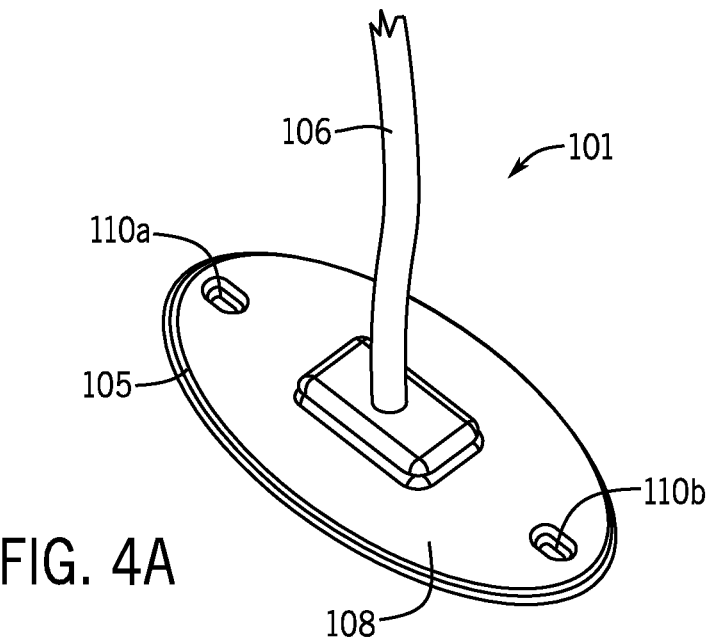
FIGS. 4A and 4B show perspective views of a locator device with a locator magnet, body, suspending member, an orientation surface and two apertures used for precise location of two targets in accordance with some embodiments of the invention.
Figure 4B:
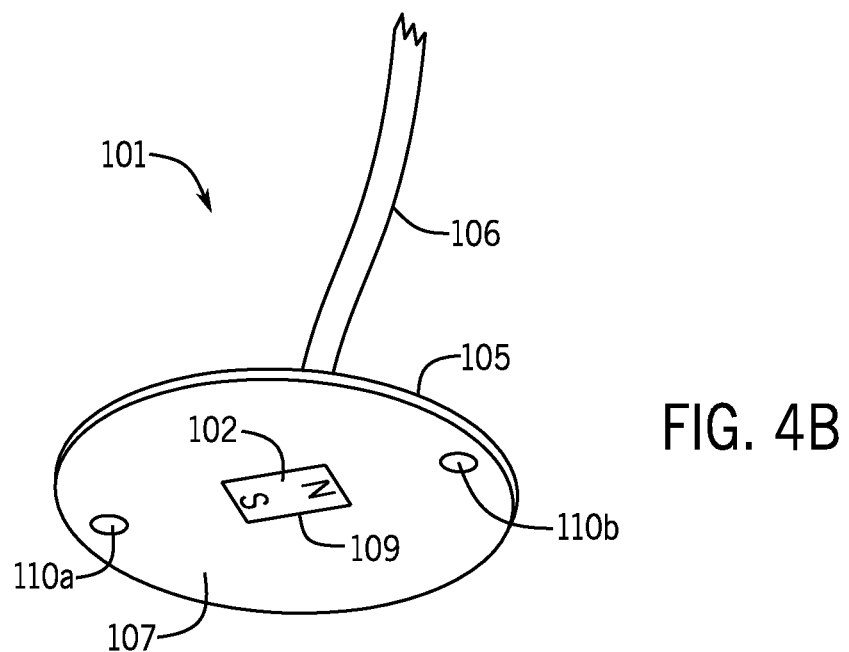
Figure 4C:
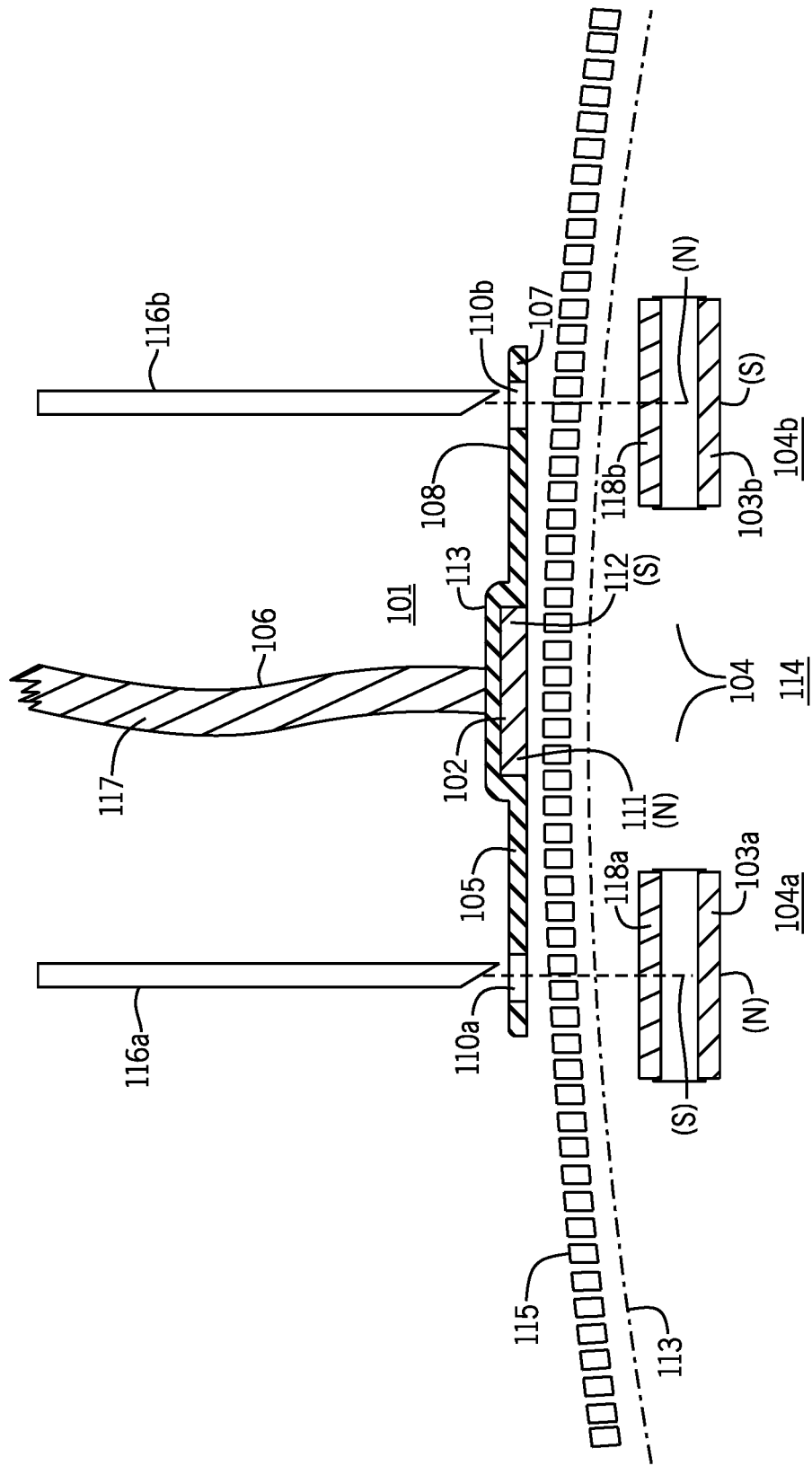
FIG. 4C shows a cross-sectional view of the locator device displayed in FIGS. 4A and 4B in use with two conventional magnetic infusion ports in accordance with some embodiments of the invention.

FIGS. 4A though 4E disclose one embodiment with combinations of features which constitute the components of locator device 101. FIGS. 4A and 4B show perspective views of a locator device 101 with a locator magnet 102 positioned coupled to body 105, suspending member 106, an orientation surface 108 and two apertures (110a, 110b) that can be used for precise location of two targets in accordance with some embodiments of the invention. FIG. 4C shows a cross-sectional view of the locator device 101 displayed in FIGS. 4A and 4B in use with two conventional magnetic infusion ports in accordance with some embodiments of the invention. The thick dashed line 115 represents tissue, and the thin dashed line 113 represents a tissue expander shell.

Figure 4D:
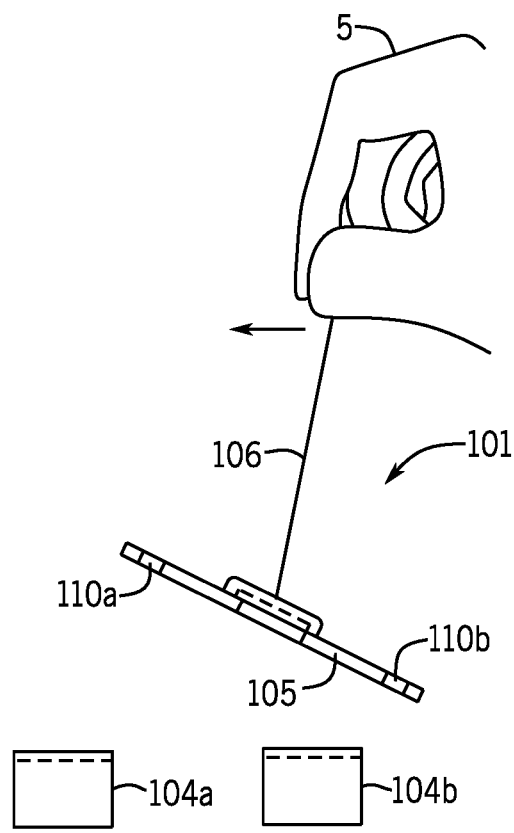
FIGS. 4D and 4E show the two different side views of the locator device from FIGS. 4A, 4B and 4C in use with a two conventional magnetic infusion ports in accordance with some embodiments of the invention.
Figure 4E:
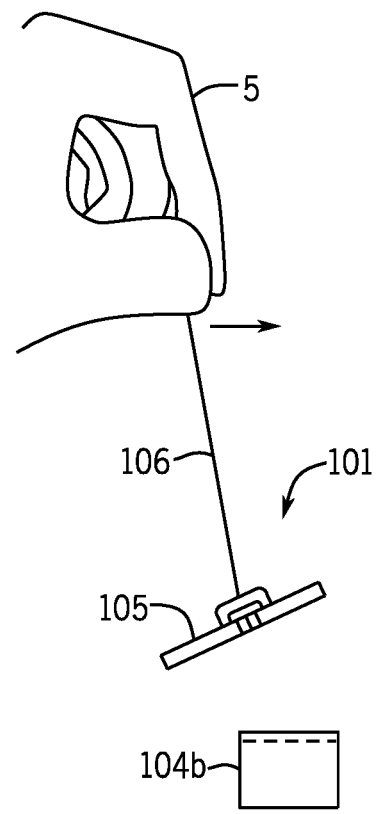

FIGS. 4D and 4E show the two different side views of the locator device 101 from FIGS. 4A, 4B and 4C in use with a two conventional magnetic infusion ports. In some embodiments, the locator device 101 is capable of accurately, precisely and concurrently locating a plurality of targets which can be tissue expander ports such as 104A and 104B, utilizing a minimum of one locator magnet 102 in the locator device 101. In some embodiments, the locator magnet 102 can be affixed to the body 105 by means of adhesive or any other conventional coupler. In some embodiments, the body 105 comprises a non-magnetic material which can be rigid or flexible. In some embodiments, the suspending member 106 can comprise a string, a chain or any other material. FIGS. 4A and 4B show the body 105 can include one generally flat surface 107 and an opposing surface 108 and a generally ellipsoidal perimeter shape. Those skilled in the art will recognize that many perimeter shapes, such as and not limited to round, square, oval, triangle, rectangle, pentagon, or any shape may achieve the intended function and do not deviate from the spirit of the invention. In some embodiments, the locator device 101 can include a recessed portion 109 on surface 107 which can be shaped to retain locator magnet 102.

FIG. 4C shows a plurality of apertures 110a and 110b extending through the body 105 from surface 107 to surface 108 which, in use, can align with the hidden targets 104a and 104b as later described. FIG. 4B shows locator magnet 102 retained within the recessed portion 109 of the body 105. In this embodiment, the locator magnet 102 comprises an elongated rectangular prism magnet, though other shapes can be used. In some embodiments, the locator magnet 102 can be polarized so that the ends 111 and 112 have opposite magnetic north and magnetic south poles as indicated in FIG. 4C. In some embodiments, on surface 108 a protrusion 113 can exist which can generally correspond in shape and location to the recessed portion 109. FIG. 4C also shows locator device 101 being used in conjunction with a representative device 114 (e.g., an implanted device) which incorporates two magnetic port targets 104. In some embodiments, each port target 104a and 104b can contain a corresponding target magnet 103a and 103b respectively, which can be magnetically aligned with the physical center of the port target. In other embodiments of the invention, the port targets may not contain magnets and instead a single target magnet can be exterior to a single or a plurality of targets. A key in this embodiment is that the target magnets 103a and 103b can be oppositely polarized such that magnetic port target 104a presents a magnetic south pole towards the skin 115 and magnetic port target 104b presents a magnetic north pole towards the skin 115, or vice versa. This allows the locator device to orientate relative to ports targets 104a and 104b using only one magnet in the locator device. In some embodiments, the attractive forces of poles 111 and 112 with the opposite poles presented by respective magnetic target magnets 103a and 103b can be used to bring locator device 101 into alignment and bring apertures 110a and 110b directly over port targets 104a and 104b. A key to the invention is that the magnetic poles and physical perimeter of locator magnet 102 do not need to align over the physical perimeter port targets 104a and 104b because the magnetic poles 111 and 112 of the locator device will align between the target magnets 103a and 103b in the implanted target device 114.

To practice the invention, the user (shown as user 5 in FIGS. 4D and 4E) can suspend locator device 101 using flexible member 106 over the proximate location of magnetic port targets 104a and 104b. Once the locator device 101 is magnetically attracted to both target magnets 103a and 103b, flexible member 106 can be used to slowly lower locator device 101 into contact with the skin 115. A key to the invention is that accurate and precise location of the subcutaneous targets is facilitated due to the geometry of the locator device 101 and more specifically a surface such as surface 108 as further described below. As illustrated in FIGS. 4D and 4E, after magnetic attraction is initiated and while lowering locator device 101 towards magnetic port target 104a and 104b, the user 5 can observe the orientation of surface 108. Apertures 110a and 110b can be in direct alignment with the port targets 104a and 104b when surface 108 is horizontal. If surface 108 tilts left, the apertures 110a and 110b are left of center of respective port targets 104a and 104b. If surface 108 tilts right, the apertures 110a and 110b are right of center of respective port targets 104a and 104b. Those skilled in the art will recognize that this holds true regardless of the direction tilt of surface 108. The user slowly moves the point of suspension 117 in the direction opposite said tilt of surface 108 until surface 108 achieves a horizontal orientation. At this point, keeping said horizontal orientation, the locator device 101 is lowered into contact with the skin 115. Once locator device 101 is in contact with the skin 115, the user can mark the skin at each aperture 110a and 110b. The locator device 101 can then be removed from the skin surface 115. In use, the physician may then pass a needle through either or both said marks and into either or both magnetic targets 104a and 104b. Alternatively, the user can pass a needle through either or both apertures 110a and 110b before locator device 101 is removed from the skin 115 surface forgoing the need for marking on the skin 115.

Figure 5A:
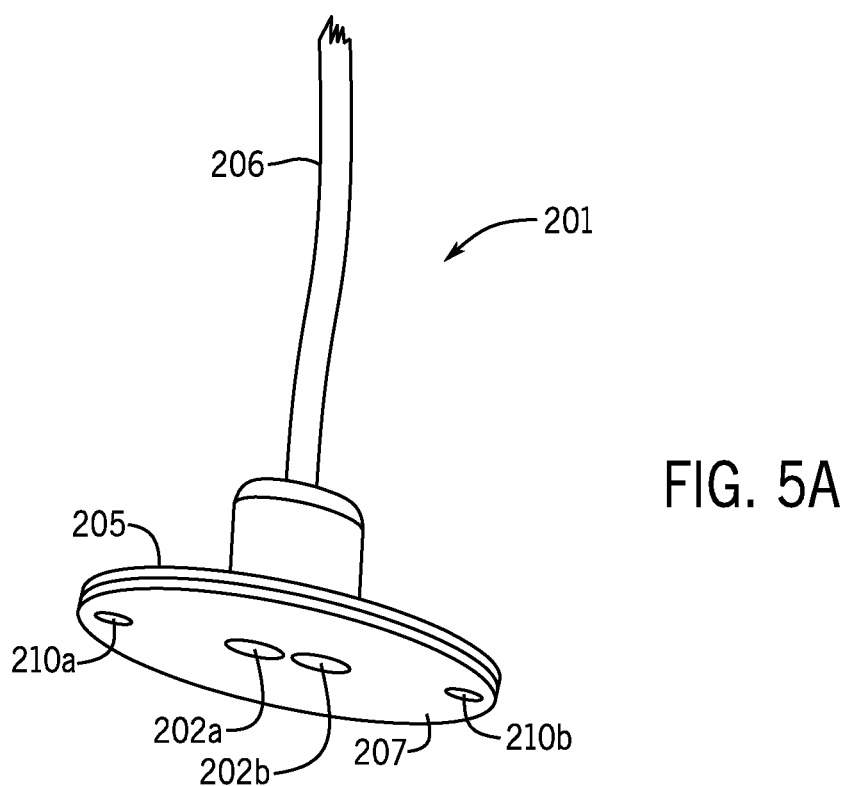
FIG. 5A shows a perspective view of a locator device with a plurality of locator magnets, a body, a suspending member, an orientation surface and two apertures used for precise location of two targets in accordance with some embodiments of the invention.
Figure 5B:
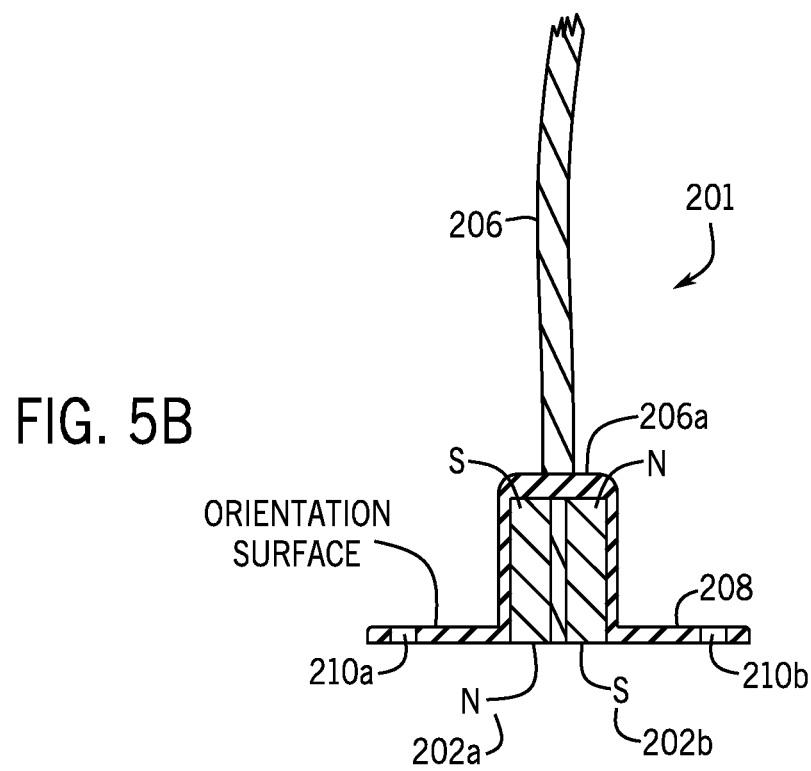
FIG. 5B shows a cross-sectional view of the locator device displayed in FIG. 5A with a plurality of locator magnets, a body, a suspending member, an orientation surface and two apertures used for precise location of two targets in accordance with some embodiments of the invention.

FIG. 5A shows a perspective view of a locator device 201 with a plurality of locator magnets 202a, 202b within body 205, a suspending member 206, an orientation surface 208 and two apertures 210a, 210b used for precise location of two targets in accordance with some embodiments of the invention. FIG. 5B shows a cross-sectional view of the locator device 201 displayed in 5A in accordance with some embodiments of the invention. In some embodiments, the locator device 201 includes suspending member 206 extending from upper surface 206a of the body 205. In some embodiments, the locator device 201 includes locator magnets 202a, 202b positioned generally centrally within the body 205 and orientation surface 208 and extending between the orientation surface 208 and the bottom surface 207. In some embodiments, the orientation surface 208. In some embodiments, the locator magnets 202a, 202b can be positioned with poles reversed with respect to each other.

Figure 6:
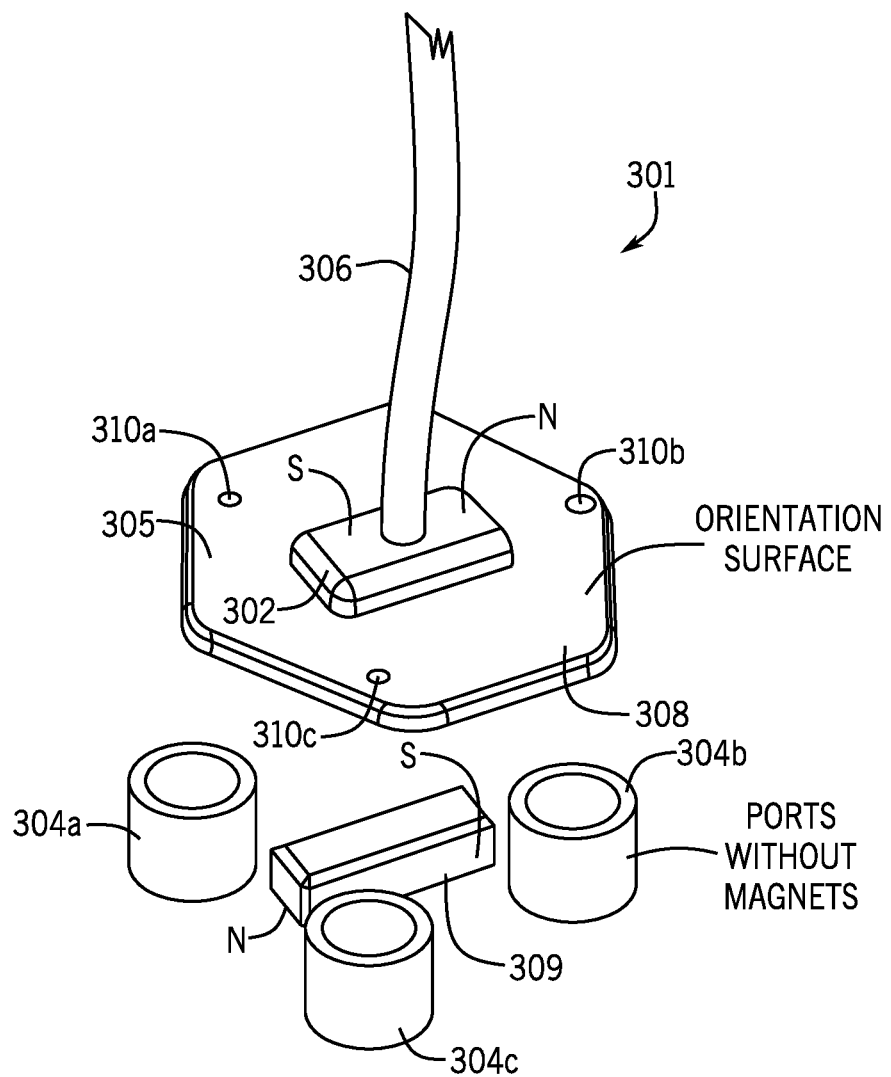
FIG. 6 shows a perspective view of a locator device with a locator magnet, a body, a suspending member, an orientation surface and a plurality of apertures used for precise location of a plurality of targets in accordance with some embodiments of the invention.

FIG. 6 shows a perspective view of a locator device 301 with a locator magnet 302, a body 305, a suspending member 306 extending from the body 305, an orientation surface 308, and a plurality of apertures 310a, 310b, 310c that can be used for precise location of a plurality of targets in accordance with some embodiments of the invention. The locator device 301 is shown in use with three unconventional non-magnetic targets (ports 304a, 304b, 304c) in accordance with some embodiments of the invention. In this non-limiting example embodiments, a single bar magnet 309 is shown, to which the locator device 301 orientates relative to, in order to locate the plurality of non-magnetic targets 304a, 304b, 304c in accordance with some embodiments of the invention. In some embodiments, the locator device 301 can be capable of accurately, precisely and concurrently locating more than two targets, utilizing a minimum of one locator magnet 302 in the locator device 301 and one target magnet 309 implanted under the skin. Those skilled in the art will realize that in other embodiments the implanted target device may include one, two, three, ten or any number of hidden targets which can be locatable using an embodiment of the invention configured to locate said hidden targets.

Some embodiments of the invention include a target location assembly that can be assembled magnetically with a locator assembly while being positioned outside of a patient's body (e.g., close to or coupled to the patient's skin). In some embodiments, a target assembly implanted in the patient can be magnetically coupled to the target location assembly. For example, FIGS. 7A-7B, and FIGS. 8A to 8D show views of a target assembly 500, and FIGS. 9A-9B, 10A-10B, and FIGS. 11-12 show views of a locator assembly 700. In use, the target assembly 500 can be subcutaneously implanted, and the locator assembly 700 can be magnetically assembled with the target assembly 500 to enable a user to locate an access port of the target assembly 500.

Figure 7A:
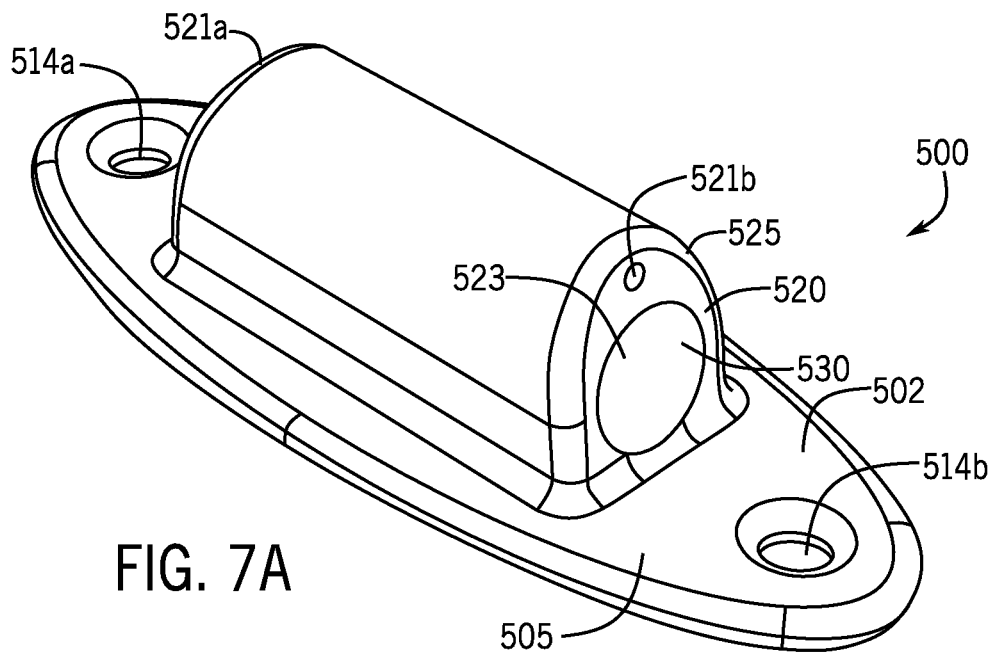
FIGS. 7A-7B illustrate perspective views of a target assembly in accordance with some embodiments of the invention.
Figure 7B:
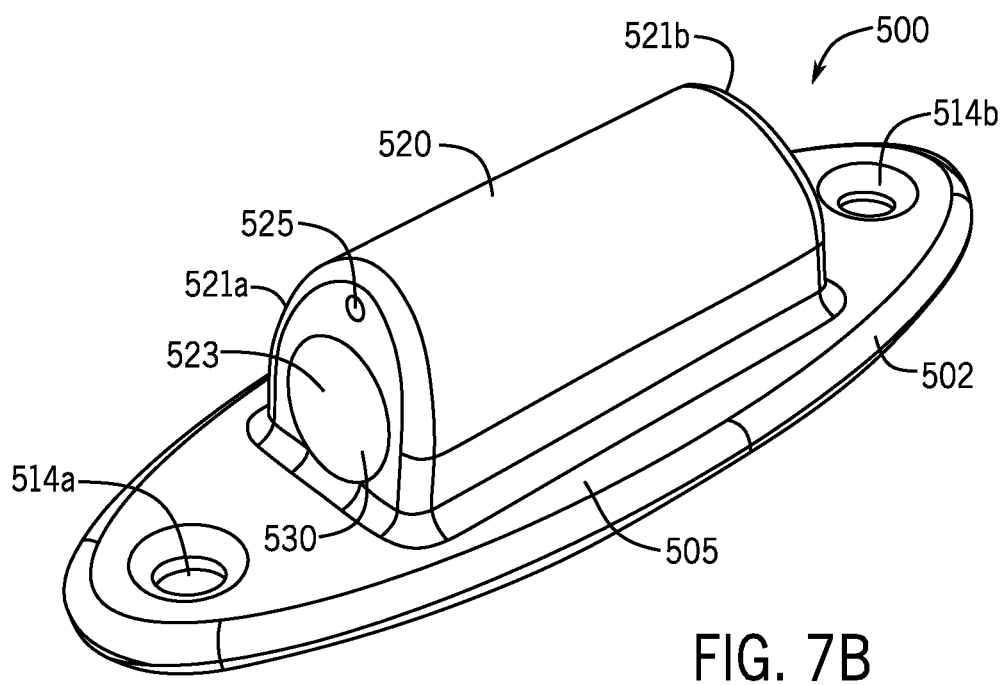
Figure 8C:
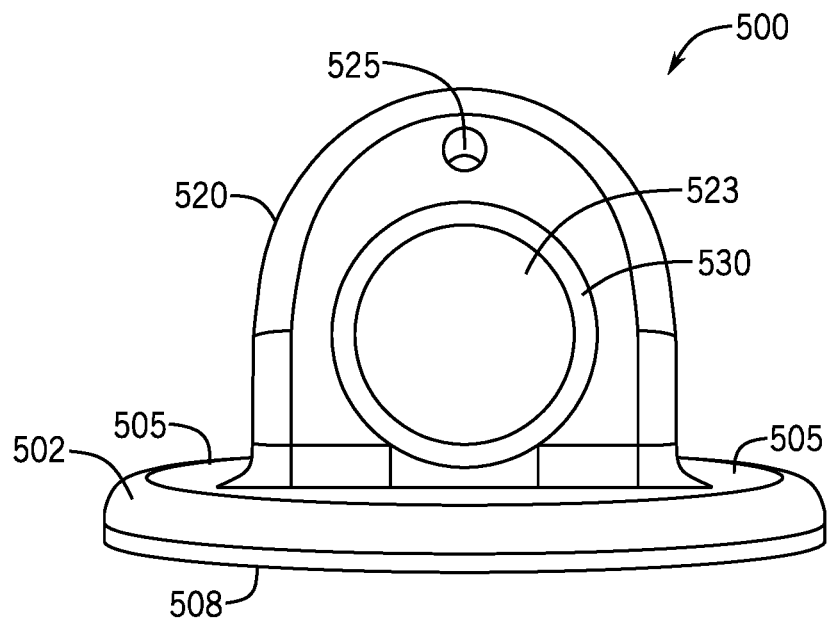
FIG. 8C illustrates an end view of the target assembly of FIGS. 7A-7B in accordance with some embodiments of the invention.
Figure 8D:
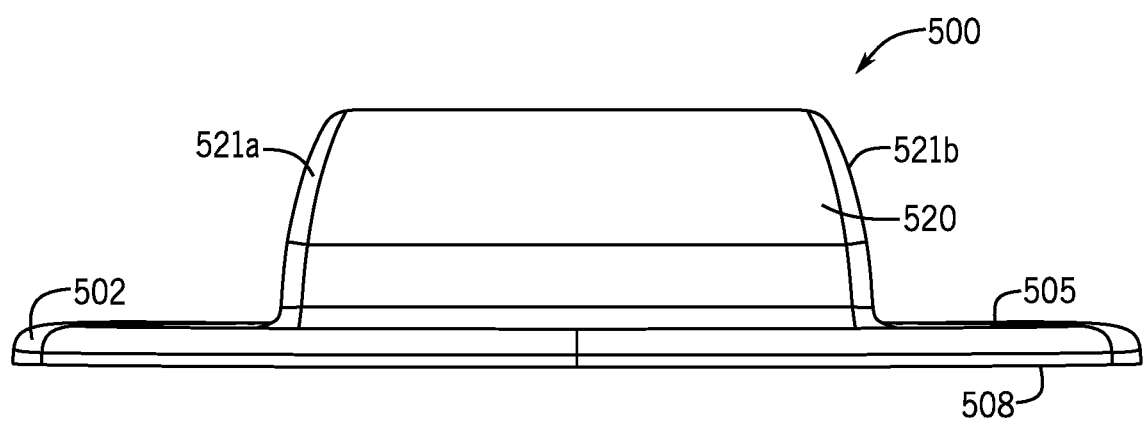
FIG. 8D illustrates a side view of the target assembly of FIGS. 7A-7B in accordance with some embodiments of the invention.

Referring to FIGS. 7A-7B, illustrating perspective views of the target assembly 500, in some embodiments, the target assembly 500 can comprise a base 505 including infusion ports 514a, 514b positioned at each end of the assembly 500. In some embodiments, base 505 can be elongated as shown and can comprise a top side 502 and a bottom side 508, with the infusion ports 514a, 514b extending through the base 505 from the top side 502 to the bottom side 508. In some embodiments, the base 505 can be ellipsoidal shaped. In other embodiments, the base 505 can be rectangular shaped. The base can be generally oblong in some embodiments of the invention. FIG. 8A illustrates a top view of the target assembly 500, and FIG. 8B illustrates a bottom view of the target assembly 500 of FIGS. 7A-7B in accordance with some embodiments of the invention. FIG. 8C illustrates an end view of the target assembly 500, and FIG. 8D illustrates a side view of the target assembly 500. In some embodiments, the base 505 can include a housing 520 coupled to and extending from the top side 502 of the base 505. In some embodiments, the housing 520 can extend from adjacent one end of the base 505 and towards an opposite end of the base 505. As shown, in some embodiments, the housing 520 can be positioned generally centrally with respect to the base 505. In other embodiments, the housing 520 can be positioned in an off-center position.

In some embodiments, the housing 520 can include a channel 523 extending from the first end 521a to the second end 521b. In some embodiments, the target assembly 500 can house at least one target magnet. For example, in some embodiments, a target magnet 530 can be positioned in the channel 523 of the housing 520 with one magnetic pole at the first end 521a of the housing 520, and a magnetically opposite pole at the second end 521b of the housing 520. In some embodiments, the target magnet 530 can extend out of either of the ends 521a, 521b. In other embodiments, the target magnet 530 can be positioned within the housing 520 within the channel 523 with no portion of the target magnet 530 extending out of the ends 521a, 521b.

In some embodiments, the housing 520 can be positioned so that the end 521a is adjacent the port 514a, and/or the second end 521b is adjacent the port 514b. In other embodiments, the housing 520 can be positioned so that the end 521a is proximate the port 514a, and/or the second end 521b is proximate the port 514b. In some further embodiments, the housing 520 can be positioned so that the end 521a abuts the port 514a, and/or the second end 521b is abuts the port 514b.

In some embodiments, the housing 520 can include a guide that can be used to positioned or move the target assembly 500. For example, some embodiments include guide 525 extending from the first end 521a of the housing 520 to the second end 521b. In some embodiments, a suspending line can be coupled to the guide 525. For example, in some embodiments, the guide 525 can comprise a channel through which the line can be threaded or positioned.

Figure 9A:
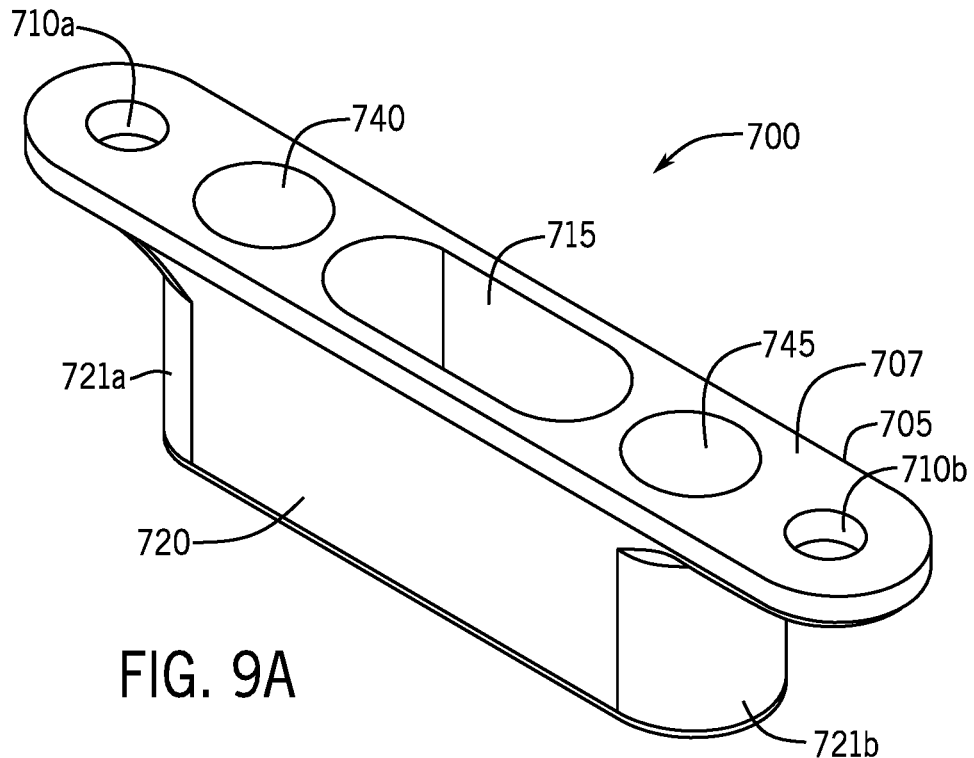
FIGS. 9A-9B illustrate perspective views of a locator assembly in accordance with some embodiments of the invention.
Figure 9B:
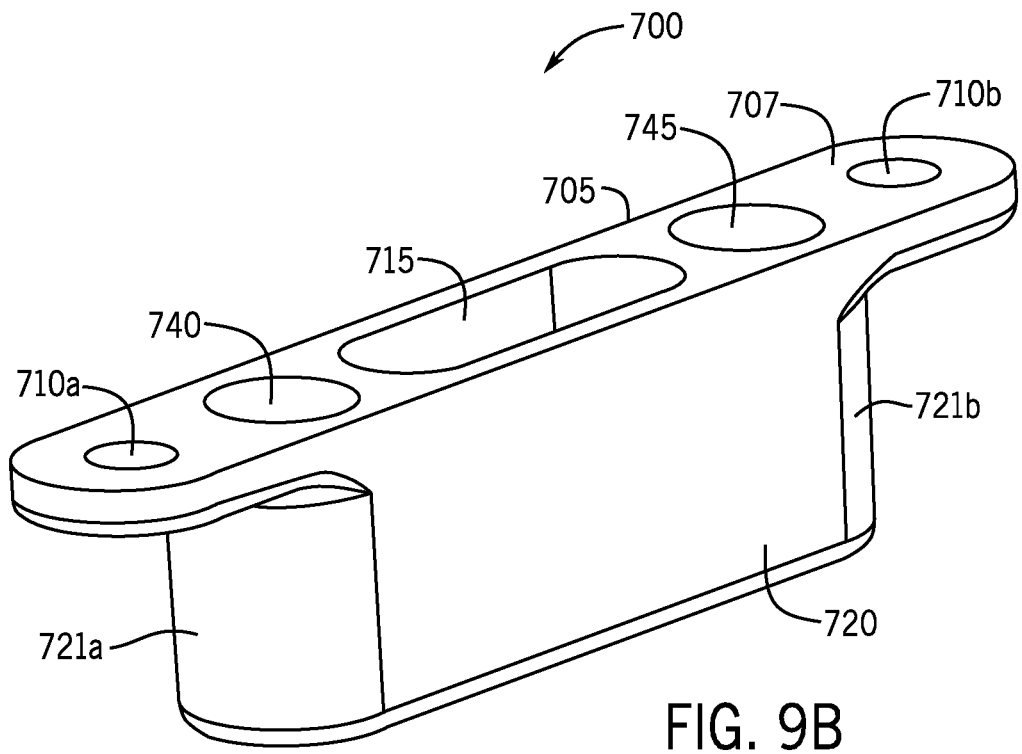
Figure 11:
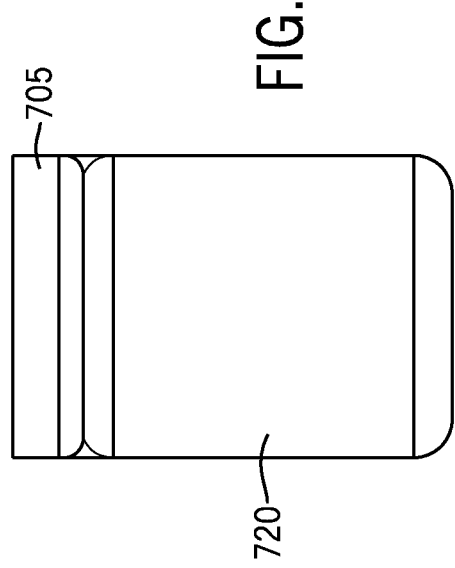
FIG. 11 illustrates an end view of the locator assembly of FIGS. 9A-9B in accordance with some embodiments of the invention.
Figure 12:
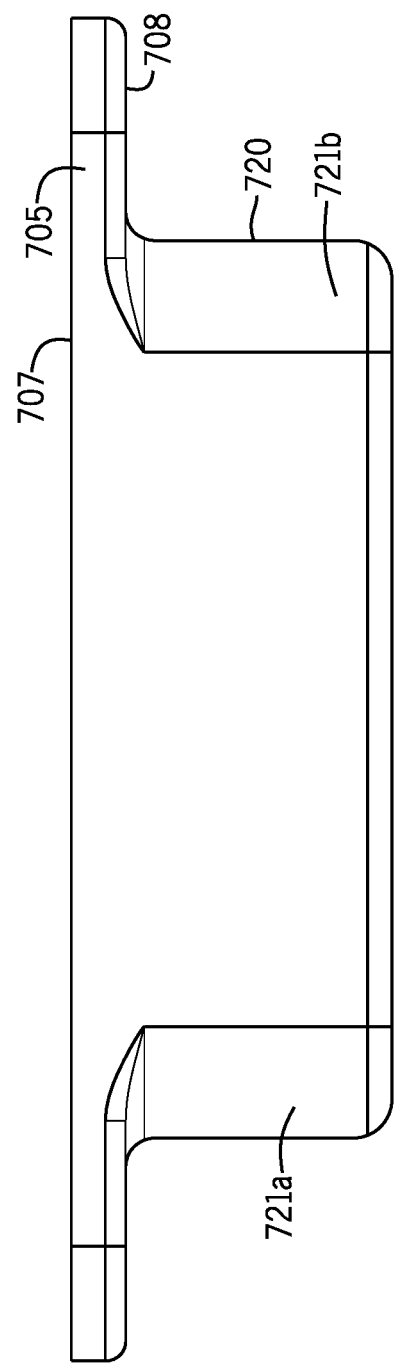
FIG. 12 illustrates a side view of the locator assembly of FIGS. 9A-9B in accordance with some embodiments of the invention.

FIGS. 9A-9B illustrate perspective views of a locator assembly 700 in accordance with some embodiments of the invention. FIG. 10A illustrates a bottom view of the locator assembly 700 of FIGS. 9A-9B, and FIG. 10B illustrates a top view of the locator assembly 700 of FIGS. 9A-9B. FIG. 11 illustrates an end view of the locator assembly 700 of FIGS. 9A-9B, and FIG. 12 illustrates a side view of the locator assembly of FIGS. 9A-9B in accordance with some embodiments of the invention. In some embodiments, the locator assembly 700 can comprise a base 705 including access apertures 710a, 710b positioned at each end of the assembly 700. In some embodiments, base 705 can be elongated as shown and can comprise a top side 708 and a bottom side 707, with the access apertures 710a, 710b extending through the base 705 from the top side 708 to the bottom side 707. In some embodiments, the base 705 can be ellipsoidal shaped. In other embodiments, the base 705 can be rectangular shaped. The base can be generally oblong in some embodiments of the invention.

In some embodiments, the base 705 can include a housing 720 coupled to and extending from the top side 708 of the base 705. In some embodiments, the housing 720 can extend from adjacent one end of the base 705 and towards an opposite end of the base 705. As shown, in some embodiments, the housing 720 can be positioned generally centrally with respect to the base 705. In other embodiments, the housing 720 can be positioned in an off-center position.

In some embodiments, the housing 720 can be positioned so that the end 721a is adjacent the aperture 710a, and/or the second end 721b is adjacent the aperture 710b. In other embodiments, the housing 720 can be positioned so that the end 721a is proximate the aperture 710a, and/or the second end 721b is proximate the aperture 710b. In some further embodiments, the housing 720 can be positioned so that the end 721a abuts the aperture 710a, and/or the second end 721b is abuts the aperture 710b.

In some embodiments, the assembly 700 can include two locator magnets 740, 745 positioned within the housing 720 adjacent each end of the housing 720. In some embodiments, the two locator magnets 740, 745 can be positioned extending at least partially into the housing 720 extending away from the base 705. In some embodiments, at least one of the two locator magnets 740, 745 can extend from the side 707 of the base 705 and into a portion of the housing 720. In other embodiments, at least one of the two locator magnets 740, 745 is positioned extending through the side 707 of the base 705. In some further embodiments, one end of at least one of the two locator magnets extends from the side 707 and away from the housing 705 (i.e., projects beyond the side 707 and is not flush with the side 707).

In some embodiments, the magnets 740, 745 can be positioned so that the magnet 740 is adjacent the aperture 710a, and/or the magnet 745 is adjacent the aperture 710b. In other embodiments, the housing 720 can be positioned so that the magnet 740 is proximate the aperture 710a, and/or the magnet 745 is proximate the aperture 710b. In some further embodiments, the housing 720 can be positioned so that the magnet 740 abuts the aperture 710a, and/or the magnet 740 abuts the aperture 710b.

Some embodiments of the invention include a cavity 715 through which can be positioned a suspension structure. For example, some embodiments include an aperture 703 coupled to the cavity 715 through which can be positioned a conventional coupler (e.g., such as a rod, and/or a string, a chain or any other material can be threaded, coupled, etc. In some embodiments, the cavity 715 can be positioned between the magnets 740, 745. In some embodiments, the cavity 715 can be positioned generally centrally between the magnets 740, 745. In some embodiments, the aperture 703 can be positioned between the magnets 740, 745. In some embodiments, the aperture 703 can be positioned generally centrally between the magnets 740, 745.

In some embodiments, the two locator magnets 740, 745 are positioned with respect to each other with reversed magnetic poles. For example, the magnet 740 can be positioned with it's magnet N-pole adjacent the side 707, and the magnet 745 can be positioned with it's magnetic S-pole adjacent the side 707. In other embodiments, the magnet 740 can be positioned with it's magnet S-pole adjacent the side 707, and the magnet 745 can be positioned with it's magnetic N-pole adjacent the side 707. This arrangement of magnets 745 can enable the assembly 700 to be aligned to the assembly 500 in a specific orientation. For example, in some embodiments, when the magnet 530 is positioned in the assembly 500 with it's N-pole adjacent the first end 521a, and the magnet 740 is positioned in the assembly 700 with it's magnet S-pole adjacent the side 707, and the magnet 745 is positioned with it's magnetic N-pole adjacent the side 707, the assemblies 500, 700 can align so that the access aperture 710a is substantially aligned with the infusion port 514a, and the access aperture 710b is substantially aligned with the infusion port 514b. Alternatively, when the magnet 530 is positioned in the assembly 500 with it's S-pole adjacent the first end 521a, and the magnet 740 is positioned in the assembly 700 with it's magnet N-pole adjacent the side 707, and the magnet 745 is positioned with it's magnetic S-pole adjacent the side 707, the assemblies 500, 700 can align so that the access aperture 710a is substantially aligned with the infusion port 514a, and the access aperture 710b is substantially aligned with the infusion port 514b.

Although only certain embodiments have been illustrated and or described, it will be apparent to those skilled in the art that various changes and modifications can be made therein without deviating from the spirit of the invention. It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. Various features and advantages of the invention are set forth in the following claims.

The invention claimed is:

1. An assembly, comprising:
 a base including a first infusion port and a target magnet housing;
 a target magnet disposed in the target magnet housing, the target magnet including a magnetic pole proximal a first side of the target magnet housing and a magnetically opposite pole proximal a second side of the target magnet housing, wherein the target magnet is separated and spaced from the first infusion port;
 a locator assembly including a locator base and a locator housing, the locator base including a first port aperture proximal a first side of the locator base and a second port aperture proximal a second side of the locator base; and
 at least two locator magnets respectively disposed at least partially within the locator housing proximal respective sides of the locator housing, the two locator magnets being separated and spaced from the first and second port apertures.

2. The assembly of claim 1, wherein the base is elongated.

3. The assembly of claim 2, wherein the elongated base is ellipsoidal shaped, rectangular shaped, or oblong.

4. The assembly of claim 1, wherein the target magnet housing is disposed proximal a center of the base.

5. The assembly of claim 1, wherein the target magnet housing is elongated.

6. The assembly of claim 1, wherein the base includes a second infusion port disposed at a side of the base opposite to a side of the base including the first infusion port.

7. The assembly of claim 1, wherein the target magnet housing includes at least one attachment aperture.

8. The assembly of claim 7, wherein the attachment aperture includes a channel extending longitudinally along the target magnet housing.

9. The assembly of claim 1, further comprising a suspending guide extending from the locator housing away from the locator base.

10. The assembly of claim 9, further comprising a suspending line coupled to the suspending guide.

11. The assembly of claim 1, wherein the at least two locator magnets are disposed with respect to each other with reversed magnetic poles.

12. A locator system comprising:
- a target base including a first infusion port proximal a side of the base;
- a target magnet coupled to the base, the target magnet including a magnetic pole, and the target magnet being separated and spaced from the first infusion port;
- a locator assembly including a locator base and a locator housing, the locator base including a port aperture proximal a side of the locator base; and
- at least two locator magnets respectively disposed proximal opposite sides of the locator housing, the locator magnets disposed with respect to each other with reversed magnetic poles, and the locator magnets being separated and spaced from the port aperture.

13. The system of claim 12, further comprising a second infusion port disposed at a side of the locator base opposite to the side of the locator base including the first infusion port.

14. The system of claim 12, further comprising a second port aperture proximal a side of the locator base opposite to the side of the locator base including the first port aperture.

15. The system of claim 12, further comprising a suspending guide extending from the locator base.

* * * * *